United States Patent [19]

Manganaro et al.

[11] 4,003,899
[45] Jan. 18, 1977

[54] PROCESS FOR RECOVERY OF CYANURIC ACID FROM TREATED CHLORINATOR MOTHER LIQUOR

[75] Inventors: James L. Manganaro, New York, N.Y.; Ronald H. Carlson, Willingboro, N.J.

[73] Assignee: FMC Corporation, Philadelphia, Pa.

[22] Filed: Sept. 25, 1975

[21] Appl. No.: 616,556

Related U.S. Application Data

[63] Continuation of Ser. No. 443,112, Feb. 15, 1974, abandoned.

[52] U.S. Cl. .................................... 260/248 A
[51] Int. Cl.² ................................ C07D 251/32
[58] Field of Search ........................ 260/248 A

[56] References Cited

UNITED STATES PATENTS

| 3,270,017 | 8/1966 | Kovalsky et al. | 260/248 |
| 3,712,891 | 1/1973 | Berkowitz et al. | 260/248 |

*Primary Examiner*—John M. Ford
*Attorney, Agent, or Firm*—Thomas B. Graham

[57] ABSTRACT

A process for recovering cyanuric acid values from a reaction mixture wherein salts of chlorinated isocyanuric acid, dichloroisocyanuric acid, and trichloroisocyanuric acid, isomers and mixtures have been formed and which have been treated to convert them to cyanuric acid values in solution, the recovery process comprising contacting the foregoing reaction mixture with an alkali metal cation in a pH range of from about 7 to about 11.

16 Claims, No Drawings

PROCESS FOR RECOVERY OF CYANURIC ACID FROM TREATED CHLORINATOR MOTHER LIQUOR

RELATED APPLICATIONS

This application is a continuation of our copending application Ser. No. 443,112, filed Feb. 15, 1974, and assigned to the assignee of the instant application, now abandoned.

Dichloroisocyanuric acid, trichloroisocyanuric acid and alkali metal and alkaline earth metal salts of dichloroisocyanuric acid, as well as hydrates, complexes or mixtures thereof, are recognized sources of available chlorine in solid bleach and detergent compositions. The most popular of these are sodium dichloroisocyanurate and potassium dichloroisocyanurate.

One method employed for preparing the foregoing chlorinated isocyanurate salts is described in U.S. Pat. No. 3,035,056. The process there disclosed involves, illustratively, reacting chlorine and an isocyanurate of an alkali metal, for example, sodium, potassium or mixtures thereof in an aqueous medium at a temperature in the range of 0° to 60° C.; the addition of reactants being substantially stoichiometric in a preferred embodiment and occuring at a pH of 6.0 to 8.5. The desired chlorinated alkali metal isocyanurate is recovered as a water wet solid by standard means such as filtration, decantation, centrifugation or the like. The patent suggests discarding the mother liquor effluent or, alternatively, subjecting it to vacuum concentration to remove a substantial amount of the water in order to induce precipitation of additional amounts of the product salts which are dissolved in the water. The remaining effluent, with its cyanuric acid values, active chlorine and chloride anion, is then discarded resulting, not only in an obvious waste of those values, but particularly in terms of the nitrogen content of these values, a pollution problem as well.

A further method described in U.S. Pat. No. 3,299,060 involves the reaction of chlorine with an alkali metal hydroxide and isocyanuric acid as a slurry in an aqueous medium at a pH of from about 6 to 7 and a temperature of about 5° to 65° C. to form the desired alkali metal dichloroisocyanurate. This method involves recovery of further product salt by filtration of the effluent and recycling some of the effluent remaining as aqueous reaction medium.

A still further method appearing in U.S. Pat. No. 2,969,360 describes the preparation of chlorinated cyanuric acids involving, in a first stage zone, the reaction of cyanuric acid, aqueous alkali and a stream of chlorine at a pH maintained between 5 and 9 and withdrawn from the first zone of a portion of the reaction mixture to a second zone in which the pH is maintained at 1.5 to 3.5. The desired dichlorocyanuric acid and trichlorocyanuric acid products are retrieved from the second zone. The pH achieved by this process, using chlorine alone, is however insufficient to effect recovery of significant amounts of cyanuric acid values remaining in the reaction mixture.

In U.S. Pat. No. 3,501,468 there is suggested, additionally, the chlorination of cyanuric acid and a mixture of sodium hydroxide and potassium hydroxide to form chloroisocyanurate complex compounds such as [(monotrichloro) tetra-(monopotassiumdichloro)] pentaisocyanurate and (monotrichloro) (monopotassiumdichloro) diisocyanurate.

The recovery of cyanuric acid from reaction product mixtures, such as described in the foregoing patents, i.e., U.S. Pat. Nos. 3,035,056, 3,299,060, 2,969,360 and 3,501,468, has been desired. Means for recovering cyanuric acid values from the effluent mother liquor occuring in the preparation of an alkali metal or alkaline earth metal salts of chloroisocyanuric acid have been proposed in copending application, Ser. No. 443,113 entitled PROCESS FOR RECOVERY OF CYANURIC ACID FROM CHLORINATED MOTHER LIQUOR, filed in the names of James Manganaro et al., now U.S. Pat. No. 3,944,548. This process involves reacting, for example, dichloroisocyanuric acid or trichloroisocyanuric acid present in the foregoing effluent with a strong mineral acid such as hydrochloric acid or sulfuric acid to induce a pH of about 0.5 to 0.8 in the mother liquor and cause the precipitation of cyanuric acid from solution. It has been found that this process while providing significant and unexpected yields of cyanuric acid values, does not exhaust the supply of these values in solutions or slurries of the mother liquor just described. Thus, the provision of means to further improve materially the recovery of these cyanuric acid values would achieve a significant advance in the state of the art.

The primary object of this invention is therefore to provide a process for recovery of cyanuric acid values from the effluent mother liquor resulting from production of chlorinated isocyanuric acids or their salts, complexes or hydrates in which the foregoing cyanuric acid values have been formed.

A further object is to provide a method which is substantially inexpensive in operation and capable, additionally, of ready application to existing plant facilities.

Various other objects and advantages of this invention will be apparent from the detailed description appearing hereinafter.

It has now been discovered, accordingly, that cyanuric acid values which have been formed in the effluent mother liquor resulting from production of dichloroisocyanuric acid, trichloroisocyanuric acid and salts of dichloroisocyanuric acid, as well as complexes, hydrates or mixtures thereof, and from which liquor available chlorine has been removed, whether by reaction of the above chlorinated isocyanurates with a strong mineral acid such as concentrated sulfuric acid or concentrated hydrochloric acid, or by other means, and which values are not otherwise precipitated out of solution, can be recovered from the treated effluent by contacting the said effluent with an alkali metal cation at a pH of from about 7 to 11 and preferably 7 to about 10.

In the process of producing dichloroisocyanuric acid, trichloroisocyanuric acid or the alkali metal or alkaline earth metal salt of dichloroisocyanuric acid, as well as hydrates, complexes or mixtures thereof as described hereinabove, and, for example, by chlorination of the corresponding salt or mixtures of salts of isocyanuric acid in an aqueous reaction medium maintained at a pH of from about 6 to about 8.5 and at a temperature of from about 0° to 60° C.; the chlorinated isocyanuric acid or its salt is precipitated from the reaction mixture as a crystal. The effluent mother liquor remaining may then, in an additional step, be contacted by, a strong mineral acid to induce a pH in the range of about 0.5 to about 0.8 in the mother liquor and effect removal of cyanuric acid values therefrom. The most prominent reaction in this step is the conversion of the dichloroisocyanuric acid as well as the corresponding trichloroisocyanuric acid to cyanuric acid, which is precipitated from the mother liquor within the foregoing pH range in significant quantities, with the conversion of available chlorine to gaseous chlorine which is evolved and removed and may be re-introduced into the process of producing the desired chlorinated isocyanurate product.

In accordance with this invention, additional and significant amounts of cyanuric acid values, as the corresponding sodium or potassium salts of cyanuric acid, may be recovered by contacting the slurry of effluent mother liquor, or the filtrate remaining after recovery of cyanuric acid values therefrom, with at least 0.5 percent of sodium or potassium ions or combinations thereof, by weight of the effluent solution, while maintaining the pH of the slurry or filtrate to within a range of about 6 to 11 and most desirably as indicated above, to about 7 to 10 and effect precipitation of a substantial portion of the cyanuric acid values which have been retained in said solution.

Where sodium cation, in the form of sodium hydroxide or sodium chloride, is employed to effect recovery, the preferred pH range of the cyanuric acid values in solution is from about 7 to 9. Where, in turn, potassium cation, in the form of potassium hydroxide or potassium chloride is employed to effect recovery the preferred pH range is from about 8 to 10. pH adjustment of the cyanuric acid values in solution is made by adding an alkali or alkaline earth metal base, preferably NaOH or KOH. Calcium hydroxide (lime), for example, is also useful in that lime is inexpensive and can be used to adjust the pH to 7 to 10.

The practice of the invention is further illustrated by reference to Table I which demonstrates the insolubility of cyanuric acid values even in dilute 5 weight percent aqueous sodium chloride solution at a pH range coming within the scope of this invention.

TABLE I

| pH* | Solubility of cyanuric acid (wt.%) in 5% NaCl solution at 25° C. |
|---|---|
| 6.3 | 0.23 |
| 7.5 | 0.08 |
| 7.8 | 0.08 |
| 9.1 | 0.07 |
| 10.1 | 0.08 |

*pH adjusted by adding 50% NaOH.

The type of effluent represented by the statement of the foregoing Table I is one, for example, resulting from the chlorination described in U.S. Pat. Nos. 2,969,360; 3,299,060; or 3,035,056 which may be first treated with a strong mineral acid, or otherwise to remove available chlorine, before being subject to treatment in accordance with this invention.

Similarly, Table II shows the relative insolubility of cyanuric acid in a 10 weight percent aqueous potassium chloride solution within the pH range of the present invention. An effluent containing a potassium chloride solution as appears in Table II results where a chlorinator effluent is derived from the chlorination described, for example, in U.S. Pat. No. 2,969,360. This effluent may be treated with a strong mineral acid before treatment with alkali metal cation according to the process of the present invention.

TABLE II

| pH* | Solubility of cyanuric acid in 10% KCl solution at 25° C. (Wt.%) |
|---|---|
| 1.1 | 0.36 |
| 2.6 | 0.37 |
| 4.1 | 0.38 |
| 5.0 | 0.31 |
| 6.5 | 0.09 |
| 8.5 | 0.04 |
| 10.7 | 0.08 |
| 12.5 | 1.88 |

*pH adjusted by adding KOH or HCl.

The decreased solubility of cyanuric acid values within the operative and preferred pH ranges of the invention is further illustrated in Table III wherein the solubility characteristics of this acid are further defined employing a mixed aqueous solution of 5 percent by weight sodium chloride and 5 percent by weight potassium chloride.

TABLE III

| pH* | Cyanuric acid solubility in 5% NaCl + 5% KCl solution at 25° C. Wt.% |
|---|---|
| 1.6 | 0.33 |
| 2.6 | 0.33 |
| 4.2 | 0.34 |
| 5.9 | 0.39 |
| 7.8 | 0.07 |
| 10.8 | 0.21 |

*pH adjusted by adding NaOH or HCl.

These compositions of Table III are repesentative of those which result from the chlorination described in U.S. Pat. No. 3,501,468. After treatment, illustratively, with a strong mineral acid, in the manner described hereinafter and subsequent neutralization with a base to the pH indicated, and in the presence of the above mixture of KCl and NaCl, the desired insolubility results.

The relative insolubilities of cyanuric acid values in a saline solution representative of those found in a chlorinator effluent in which cyanuric acid values have been formed and not removed from the solution prior to neutralization according to the invention and in distilled water are shown in the graph on the accompanying drawing. The unexpected insolubility of cyanuric acid within the pH range of the invention in saline solution, e.g., 10 weight percent of sodium chloride in water, is particularly evident in view of the tendency of cyanuric acid to demonstrate an increased solubility in distilled water solution within the pH range of the invention.

While not wishing to be limited to any particular theory of operation with respect to the invention described herein it is believed that the relative insolubility of cyanuric acid in saline solution indicated by the significant dip shown in the drawing at the elevated pH range occurring above 5 and below 11 can be explained by the conversion of unionized cyanuric acid to the singly charged anion which then has to satisfy the following solubility criteria at 25° c.

$$(Na^+)(H_2Cy^-) = 3.55 \times 10^{-4}$$

$$(Na^+)^2(HCy^=) = 1.45 \times 10^{-1}$$

$$(Na^+)^2(Cy^=) = 7.38$$

*Cyanuric acid moiety

The term "alkali metal salts" as employed herein is understood to encompass not only sodium and potassium salts of the acids specified but, by way of illustration, those of lithium and cesium, as well. The term "alkaline earth metal salts" is intended, in like manner, to include within its scope, for example, the barium, magnesium and calcium salts of the particular acids recited.

The inorganic acids characterized generally as strong mineral acids employed in treatment of the chlorinator effluent prior to neutralization in accordance with one preferred embodiment described herein are those inorganic acids having a dissociation constant greater than that of acetic acid.

These mineral acids include sulfuric acid, nitric acid, hydrochloric acid, and although less preferred, phosphoric acid. The most desirable are hydrochloric acid and sulfuric acid.

While it is not intended that any particular theory or principle be relied upon, it is believed that the function of the mineral acid on the waste liquor prior to neutralization thereof according to the invention may be explained by the following series of equations in which dichloroisocyanuric acid is referred to as DCCA and cyanuric acid as CA:

1(a) DCCA + 2H$_2$O $\rightleftharpoons$ CA + 2HOCl

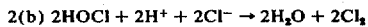

2(b) 2HOCl + 2H$^+$ + 2Cl$^-$ → 2H$_2$O + 2Cl$_2$

The overall reaction may thus be expressed as follows:

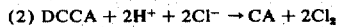

(2) DCCA + 2H$^+$ + 2Cl$^-$ → CA + 2Cl$_2$

The Cl ion is normally present as a result of the prior chlorination reaction and its concentration may be enhanced, if desired, by HCl, NaCl or other Cl ion sources. If no Cl ion is present it may be added to the mother liquor.

According to this theory or principle the addition of hydrochloric acid, used illustratively in the foregoing equations, induces the formation of chlorine as a result of the reaction of the hydrochloric acid reagent with the hypochlorous acid existing in equilibrium in equation 1 (a). Removal of this chlorine drives the equilibrium of each of the foregoing equations to the right, with the resulting formation of increased concentrations of cyanuric acid in equation 1 (a) as well as further gaseous chlorine in equation 1 (b), and an overall reaction, as indicated, in equation (2). This results in reducing or eliminating available chlorine from the waste liquor.

In order to secure initial precipitation of cyanuric acid from the effluent, it is essential that the pH be within the range of about 0.5 to 0.8. The cyanuric acid thus produced manifests a solubility lower than that of dichloroisocyanuric acid and will separate out of solution at the concentrations that the cyanuric acid normally attains, which is in the range of 0.3 to 2 percent by weight in the foregoing mother liquor, and under the other operative conditions obtaining in the reactor; namely, the concentration of the alkali metal or alkaline earth metal chlorides, or mixtures thereof, present in the aqueous medium of the effluent, usually about 6 to 10 percent by weight of the total effluent, and at a temperature within the range of 5° to 40° C. and usually about 25° C.

Maintenance of the pH within the parameters of 0.5 to 0.8 provides a ratio of about 2.0 to 4.0 of mineral acid equivalents per mole of cyanuric acid.

The recovery process is undertaken in a closed reaction vessel at a pressure which is not narrowly critical, and may, for example, be atmospheric, one of reduced pressure or that resulting from an air sparge of the reaction vessel during the recovery reaction. While not critical to the result secured, therefore, the use of reduced pressure, e.g., as little as 0.7 psia, has been found to be preferred.

A batch or continuous operation is feasible so long as an effective residence time for reaction of mineral acid and effluent of at least 0.2 hour in a reactor alone, or in combination with a product receiver vessel, is achieved. Longer residence times to several hours may be used if they can be tolerated in the plant operation. Generally 0.2 to 1 hour is enough.

The cyanuric acid precipitated in the reactor or, if desired, in a separate product recovery vessel, is removed as indicated, in the form of a slurry to a solid-liquid separation vessel, e.g. filter, centrifuge, or the like, wherein the cyanuric acid is recovered in crystalline form.

Thus after the recovery reaction with mineral acid has run its course, or has been otherwise terminated, the pH of the reaction vessel having been maintained at between 0.5 to 0.8 for a period of from 0.2 or, if desired, 0.5 to 2.0 hours, the initial solid cyanuric acid values may be recovered by filtration of the reactor effluent or the effluent containing all the foregoing solids.

It is immediately before or after this separation step that recovery of the further significant cyanuric acid values according to the present invention, as embodied in the alkali or alkaline earth metal salts of cyanuric acid, primarily as the mono-substituted salt of cyanuric acid, e.g., hydrated monosodium cyanurate, is effected. The recovery of these further cyanurate values is effected according to the invention by treatment of the reactor effluent to neutralize it to a pH of about 7 to 11 and preferably, as previously indicated, from about 7 to about 10, with sequential filtration and recovery of the corresponding alkali metal salts of cyanuric acid formed in the alkaline, saline medium of the mother liquor. The filtrate, from which substantially all of the cyanuric acid values have been removed, may be discarded.

The neutralizing pH of this second recovery phase constituting the process of the invention is normally complete in 5 to 180 minutes. The mole ratio of alkali or alkaline earth metal hydroxide, e.g., sodium hydroxide, to cyanuric acid in this latter neutralizing step is approximately about 1:1 at the stated pH. This neutralization step can follow filtration of the effluent maintained at a pH of 0.5 to 0.8 after removal of the cyanuric acid solids therefrom and is completed in from 5 to 180 minutes. In this neutralization process the salts of cyanuric acid are recovered as crystals by a second filtration or equivalent operation; the filtrate remaining being then discarded.

In an alternative procedure the neutralizing alkali metal or alkaline earth hydroxide is added before filtration and removal of cyanuric acid. The concentration of the foregoing hydroxide, i.e., a mole ratio of hydroxide to cyanuric acid of 1.0 and the consequent pH of 7 to 11 are substantially identical to the conditions provided when neutralization of effluent is effected after filtration and removal of cyanuric acid except that a longer residence time, i.e., 5 to 300 minutes, may be used in the neutralization step.

The following examples are further illustrative of the invention. In these examples all parts and percentages (%) are by weight unless otherwise expressly indicated.

EXAMPLE 1

This example illustrates the recovery of cyanuric acid in a first step and further cyanuric acid values from the neutralized filtrate remaining after removal of the foregoing cyanuric acid in a second step, according to the invention.

Three kilograms of synthetically prepared dichloroisocyanuric acid mother solution which synthetic mixture results typically from the reaction in an aqueous solution of a pH of 1.5 to 3.5 of substantially stoichiometric amounts of chlorine and disodium isocyanurate and having the following listed analysis, was fed to a reactor at a steady rate of 39 cc/min.

Analysis:
2.3% (or 69 grams dichloroisocyanuric acid)
10.0% (or 300 grams) NaCl
87.7% (or 2631 grams) $H_2O$ The reactor was a 1000 cc reaction pot sealed for operation at reduced pressure. The working volume was about 550 cubic centimeters. A magnetic stirrer was used to agitate the reactor contents. In this example both the reactor and product receiver vessel (to which the reactants were transferred when the addition of reactants was completed) were maintained at reduced pressure. Agitation did not however take place in the product receiver vessel.

The operating conditions are recited in Table IV as follows:

TABLE IV

|  | Reactor | Product Receiver Vessel |
|---|---|---|
| Temperature, ° C | 26 | 12 |
| pH | 0.62 | 0.62 |
| Residence Time, Min. | 14 | 56 |
| Pressure, psia. | 2.1 | 2.1 |

The mole ratio of hydrochloric acid to cyanuric acid was found to be 3.2 (theory is 2.0). After acidification at the conditions given above, the precipitated cyanuric acid was filtered off and dried. The precipitate is designed "Solids I" in Table V appearing hereinafter. The filtrate was analyzed and found to have 0.56% cyanuric acid and 0.07% available chlorine. This filtrate was then neutralized with 50% NaOH to raise the pH from 0.62 to 9.1. The temperature increased from 14° to 18° C. Solids precipitated in the pH range 7.0 to 9.0. The slurry was allowed to stir for 10 minutes and then filtered. These solids which are called Solids II in Table V were then dried. The filtrate from the neutralization analyzed 0.17% cyanuric acid and 0.06% available chlorine.

The data on Solids I and II are given below:

TABLE V

|  | SOLIDS I | SOLIDS II |
|---|---|---|
| Wt., grams | 26.3 | 16.7 |
| %CA* | 99.6 | 74.0 |
| Wt. of CA* in solids, grams | 26.2 | 12.4 |
| Average (%Cl) | 1.8 | 0.2 |

*Cyanuric acid equivalent

Adding the cyanuric acid of Solids I and the cyanuric acid values of Solids II, a total cyanuric acid recovery in terms of cyanuric acid of 85.8% was obtained. The remaining cyanuric acid values remained in the filtrate. No cyanuric acid was decomposed.

EXAMPLE 2

This example illustrates the neutralization of treated effluent chlorinator mother liquor according to the practice of the invention but replacing in the step preliminary to neutralization the concentrated hydrochloric acid of Example 1 with concentrated sulfuric acid.

In this example, the amount, feed rate and composition of synthetically derived dichloroisocyanuric acid containing mother liquor was the same as described in Example 1. The reactor was also the same as previously described. Concentrated $H_2SO_4$ (96%) replaced the hydrochloric acid.

The operating conditions employed were as recited in Table VI.

TABLE VI

|  | Reactor | Product Receiver Vessel |
|---|---|---|
| Temperature, ° C. | 26 | 26 |
| pH | 0.65 | 0.65 |
| Residence time, min. | 14 | 56 |
| Pressure, psia | 0.77 | 0.77 |

The mole ratio of concentrated $H_2SO_4$ to cyanuric acid content was found to be 1.7 (theory is 1.0). The amount of unwashed but dried cyanuric acid recovered was 30.8 grams and assayed 97.8% cyanuric acid. This represents an initial recovery of 67.0%. The filtrate from this initial filtering was then neutralized with 51.6 grams of 50% NaOH to a pH of 8.1 and allowed to stir for 10 minutes. The solids precipitating out of solution were filtered off and the filtrate discarded. These dried solids, which weighed 13.6 grams, have the following analysis:

% cyanuric acid equivalent 70.2
% Na 17.9
% $H_2O$ 8.6
% Chloride 3.6

The total of recovered cyanuric acid values was thus 88.3%. The cyanuric acid values lost were lost as soluble cyanuric acid in the filtrate.

EXAMPLE 3

This example illustrates the practice of the invention incorporating a mother liquor effluent type of composition containing potassium dichloroisocyanurate and potassium chloride.

In this example, the amount of synthetically prepared but typical dichloroisocyanuric acid containing mother liquor was the same as in Example 1. The equipment utilized was also the same. The synthetic mother liquor differed from that of Example 1, however, in having the following composition:

Potassium dichloroisocyanurate 2.74% or 82.32 grams

Potassium chloride 11.93% or 357.9 grams

Hydrochloric acid 1.14% or 34.2 grams at 37% weight concentration

Water 84.19% or 2525.7 grams

The foregoing mixture is typical of that which would result if chlorination to produce dichloroisocyanuric acid were performed with a feed containing potassium hydroxide to cyanuric acid in a mole ratio 2 to 1 respectively. The foregoing mother liquor composition was treated with hydrochloric acid in a mole ratio of this latter acid to cyanuric acid of 3.51 to 1 respectively (theory is 2.0 to 1 respectively). The feed rate to the reactor vessel of mother liquor composition was 102 milliliters per minute. The operating conditions were as recited in Table VII.

TABLE VII

| | Reactor | Product Receiver Vessel |
|---|---|---|
| Temperature, ° C. | 19 | 15 |
| pH | 0.5 | 0.5 |
| Residence time, minutes | 5.4 | 21.4 |
| Pressure, pounds per square inch absolute | 0.77 | 0.77 |

The amount of dried cyanuric acid recovered was 19.0 grams which analyzed for a content of 98.3 percent cyanuric acid. This represented a recovery of 41.5 percent. The filtrate from this initial filtering was then treated in a manner sililar to that described in Example 2. Specifically the filtrate was neutralized with 50% NaOH to pH = 9.0, and allowed to stir for 10 minutes. The solids precipitating out of solution were filtered off and dried. These solids, weighing 27.0 grams, upon analysis indicated 64.75% cyanuric acid and represented a cyanuric acid value recovery of 38.9% to bring the total to 80.4%. After neutralization the cyanuric acid level in solution was reduced to 0.22%.

The complete analysis of the solids recovered after neutralization was performed and the following characterization found:

| | |
|---|---|
| 64.75% | CA* |
| 20.75% | K |
| 1.87% | Na |
| 6.2% | Cl |
| 9.1% | $H_2O$ |

*cyanuric acid equivalent

This analysis indicates the cyanuric acid present to be principally in the form of monopotassium cyanurate monohydrate. The mole ratio of K to cyanuric acid values was 1.05.

It will be evident that the terms and expressions which have been employed are used as terms of description and not of limitation. There is no intention in the use of such terms and expressions of excluding equivalents of the features shown and described or portions thereof and it is recognized that various modifications are possible within the scope of the invention claimed.

What is claimed is:

1. In a process for recovering cyanuric acid values from the group consisting of cyanuric acid and alkali metal salts thereof and mixtures thereof, isomers and salts, said cyanuric acid values being present in aqueous solution in an effluent mother liquor produced in the preparation of chlorinated isocyanuric acids and salts thereof, and from which mother liquor available free chlorine has been removed by acidification, the improvement, comprising contacting said effluent mother liquor with aqueous solution of alkali metal cation selected from the group consisting of sodium and potassium, in amounts sufficient to effect precipitation of said cyanuric acid values as corresponding salt from said effluent mother liquor at a pH within the range of about 7 to about 11.

2. The process of claim 1 wherein said effluent mother liquor contains a precipitate of chlorinated isocyanuric acids and salts thereof.

3. The process of claim 1 wherein said effluent mother liquor contains a precipitate of said cyanuric values prior to treatment with alkali metal cation.

4. The process of claim 1 wherein said effluent mother liquor is substantially free of precipitate.

5. The process of claim 1 wherein said alkali metal cation is present in an amount by weight of at least 3 percent of said effluent mother liquor.

6. The process of claim 5 wherein said alkali metal cation is sodium.

7. The process of claim 5 wherein said alkali metal cation is potassium.

8. The process of claim 5 wherein said alkali metal cation is a mixture of sodium and potassium.

9. The process of claim 5 wherein said sodium is present in said effluent mother liquor at a pH of from about 7 to about 9.

10. The process of claim 5 wherein said potassium is present in said effluent mother liquor at a pH of from about 8 to about 10.

11. The process of claim 5 wherein said sodium is present in an aqueous solution as sodium hydroxide.

12. The process of claim 5 wherein potassium is present in aqueous solution as potassium hydroxide.

13. The process of claim 5 wherein said sodium is present in an aqueous solution as sodium chloride.

14. The process of claim 5 wherein said potassium is present in an aqueous solution as potassium chloride.

15. The process of claim 1 wherein said isocyanurates in said mother liquor have been chlorinated to provide the corresponding chlorinated isocyanuric acids selected from dichloroisocyanuric and trichloroisocyanuric acids.

16. The process of claim 1 wherein said isocyanurates in said mother liquor have been chlorinated and neutralized to provide the corresponding chlorinated isocyanurate salts selected from the group consisting of sodium dichloroisocyanurate and potassium dichloroisocyanurate.

* * * * *